United States Patent [19]
Johnson et al.

[11] 4,154,949
[45] May 15, 1979

[54] 11-DESOXY-15-SUBSTITUTED-ω-PENTA-NORPROSTAGLANDINS

[75] Inventors: Michael R. Johnson, Gales Ferry; Thomas K. Schaaf, Old Lyme; Jasjit S. Bindra, Groton; Hans-Jurgen E. Hess, Old Lyme; James F. Eggler, Stonington, all of Conn.

[73] Assignee: Pfizer Inc., New York, N.Y.

[21] Appl. No.: 763,811

[22] Filed: Jan. 31, 1977

Related U.S. Application Data

[63] Continuation-in-part of Ser. No. 531,676, Nov. 11, 1974, abandoned.

[51] Int. Cl.$^2$ ............................................. C07C 177/00
[52] U.S. Cl. ............................... 560/53; 260/340.5 P; 562/463
[58] Field of Search ........................ 560/53; 562/463; 260/340.5

[56] References Cited

U.S. PATENT DOCUMENTS 3,971,826   7/1976   Hess et al. ....................... 260/520 B

OTHER PUBLICATIONS

38270V/21 (Be 807,047), Derwent Abstract (08-11-72).

*Primary Examiner*—Paul J. Killos
*Attorney, Agent, or Firm*—Connolly and Hutz

[57] ABSTRACT

11-desoxy-15-substituted-ω-pentanorprostaglandins and various intermediates employed in their preparation. The novel prostaglandins of this invention have been found to have activity profiles comparable to the parent prostaglandins, but exhibit a greater tissue specificity of action.

5 Claims, No Drawings

11-DESOXY-15-SUBSTITUTED-ω-PENTANOR-PROSTAGLANDINS

CROSS-REFERENCE TO RELATED APPLICATION

This application is a continuation-in-part of co-pending United States patent application Ser. No. 531,676 filed Dec. 11, 1974.

BACKGROUND OF THE INVENTION

This invention relates to certain novel analogs of the naturally occurring prostaglandins. In particular, it relates to novel 11-desoxy-15-substituted-ω-pentanor-prostaglandins and various novel intermediates useful in their preparation.

The prostaglandins are C-20 unsaturated fatty acids which exhibit diverse physiological effects. For instance, the prostaglandins of the E and A series are potent vasodilators (Bergstrom, et al., Acta Physiol. Scand. 64:332–33, 1965 and Bergstrom, et al., Life Sci. 6:449–445, 1967) and lower systemic arterial blood pressure (vasodepression) on intravenous administration (Weeks and King, Federation Proc. 23:327, 1964; Bergstrom, et al., 1965, op. cit.; Carlson, et al., Acta Med. Scand. 183:423–430, 1968; and Carlson, et al., Acta Physiol. Scand. 75:161–169, 1969). Another well known physiological action for $PGE_1$ and $PGE_2$ is as a bronchodilator (Cuthbert, Brit. Med. J. 4:723–726, 1969).

Still another important physiological role for the natural prostaglandins is in connection with the reproductive cycle. $PGE_2$ is known to possess the ability to induce labor (Karim, et al., J. Obstet. Gynaec. Brit. Cwlth. 77:200–210, 1970), to induce therapeutic abortion (Bygdeman, et al., Contraception, 4, 293 (1971) and to be useful for control of fertility (Karim, Contraception, 3, 173 (1971)). Patents have been obtained for several prostaglandins of the E and F series as inducers of labor in mammals (Belgian Patent No. 754,158 and West German Patent No. 2,034,641), and on $PGE_1$, $F_2$ and $F_3$ for control of the reproductive cycle (South African Patent No. 69/6089). It has been shown that luteolysis can take place as a result of administration of $PGF_{2\alpha}$[Labhsetwar, Nature, 230, 528 (1971)] and hence prostaglandins have utility for fertility control by a process in which smooth muscle stimulation is not necessary.

Still other known physiological activities for $PGE_1$ are in the inhibition of gastric acid secretion (Shaw and Ramwell, In: Worchester Symp. on Prostaglandins, New York, Wiley, 1968, p. 55–64) and also of platelet aggregation (Emmons, et al., Brit. Med. J. 2:468–472, 1967).

It is now known that such physiological effects will be produced in vivo for only a short period, following the administration of a prostaglandin. Evidence indicates that the reason for this rapid cessation of activity is that the natural prostaglandins are quickly and efficiently metabolically deactivated by β-oxidation of the carboxylic acid side-chain and by oxidation of the 15α-hydroxy group (Anggard, et al., Acta. Physiol. Scand. 81, 396 (1971) and reference cited therein). It has been shown that placing a 15-alkyl group in the prostaglandins has the effect of increasing the duration of action possibly by preventing the oxidation of the C15-hydroxyl [Yankee and Bundy, JACS 94, 3651 (1972)], Kirton and Forbes, Prostaglandins, 1, 319 (1972).

11-desoxy-15-substituted prostaglandins of the $E_1$ and $E_2$ series are disclosed in Netherlands Patent 730 1094, including the 15-alkyl and 15-benzyl compounds.

It was, of course, considered desirable to create analogs of the prostaglandins which would have physiological activities equivalent to the natural compounds, but in which the selectivity of action and the duration of the activity would be increased. Increased selectivity of action would be expected to alleviate the severe side effects, particularly gastrointestinal side effects frequently observed following systemic administration of the natural prostaglandins (Lancet, 536, 1971).

SUMMARY OF THE INVENTION

The present invention provides 11-desoxy-15-substituted-ω-pentanorprostaglandins having superior activity as hypotensive agents.

The compounds of the present invention of the $E_0$ series are represented by the formula:

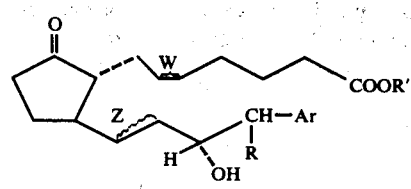

wherein Ar is α- or β-naphthyl; phenyl; 3,4-dimethoxyphenyl; 3,4-methylenedioxyphenyl; 3,4-dichlorophenyl; 3,5-dimethyl and monosubstituted phenyl wherein said substituent is bromo, chloro, fluoro, trifluoromethyl, phenyl, lower alkyl or lower alkoxy; R is hydrogen;

and wherein R' is hydrogen;

alkyl of from 1–10 carbon atoms, aralkyl of from 7 to 9 carbon atoms; α- or β-naphthyl; phenyl or substituted phenyl wherein said substituent is lower alkyl, lower alkoxy, chloro, bromo, fluoro or phenyl and wherein W is a single bond; and Z is a single bond.

A preferred compound of this formula is 11-desoxy-16-phenyl-ω-tetranorprostaglandin $E_0$.

Compounds of the present invention of the 13,14-dihydro-$E_2$ series are represented by the formula:

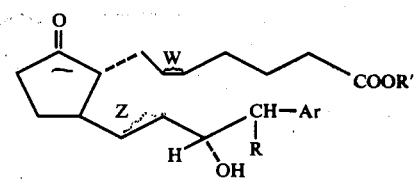

wherein Ar, R and R' are as defined above
and W is a cis double bond and Z is a single bond.

A preferred compound of this formula is 11-desoxy-13,14-dihydro-16-phenyl-ω-tetranorprostaglandin $E_2$.

In addition, certain optically active 15-epi-11-desoxy-16-Ar-substituted-ω-tetranorprostaglandin $E_2$ compounds have superior properties as hypotensive agents. A preferred compound is the optically active 15-epi-11-desoxy-16-(m-tolyl)-ω-tetranorprostaglandin $E_2$, having the structure.

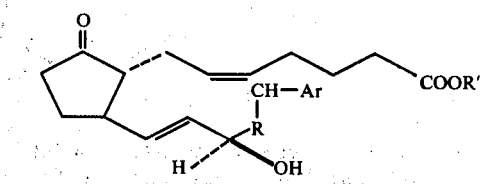

wherein Ar is m-tolyl and R and R' are each hydrogen.

DETAILED DESCRIPTION OF THE INVENTION

As shown in Scheme A, the first step (1→2) is a condensation between the known aldehyde 1 (Corey and Ravindranathan, *Tetrahedron Lett.*, 1971, 4753 with an appropriate 3-keto phosphonate to produce enone 2. The keto phosphonate is usually produced by condensation of the appropriate carboxylic acid ester with a dialkyl methyl phosphonate. Typically the desired methyl ester is condensed with dimethyl methyl phosphonate.

Enone 2 is then reduced to enol 3 with zinc borohydride or a hindered alkyl borohydride such as lithium triethylborohydride or potassium tri-sec-butylborohydride. This reduction produces a mixture of epimers both of which may be used as substrates for further reactions. The 3 is used to produce prostaglandin analogs having a α-hydroxyl at $C_{15}$. The epimer of 3 is used to produce prostaglandin analogs having a β-hydroxyl at $C_{15}$. In addition, the mixture of $C_{15}$ epimers may be used to produce 15-keto prostaglandin analogs. The epimers produced in the hydride reduction can be separated by column, preparative thin layer, or preparative high pressure liquid chromatography. In the reduction reaction ethers such as tetrahydrofuran or 1,2-dimethoxyethane of acetonitrile are usually employed as solvents.

Enone 2 may be reduced catalytically with hydrogen to ketone 6, a suitable starting material for the preparation of 13,14-dihydro prostaglandin analogs of the present invention. This reduction may be achieved with either a homogeneous catalyst such as tris-tri-phenyl-phosphinerhodiumchloride or with a heterogeneous catalyst system such as platinum, palladium or rhodium. The stage at which the reduction is carried out is not critical as will be seen below.

Scheme A

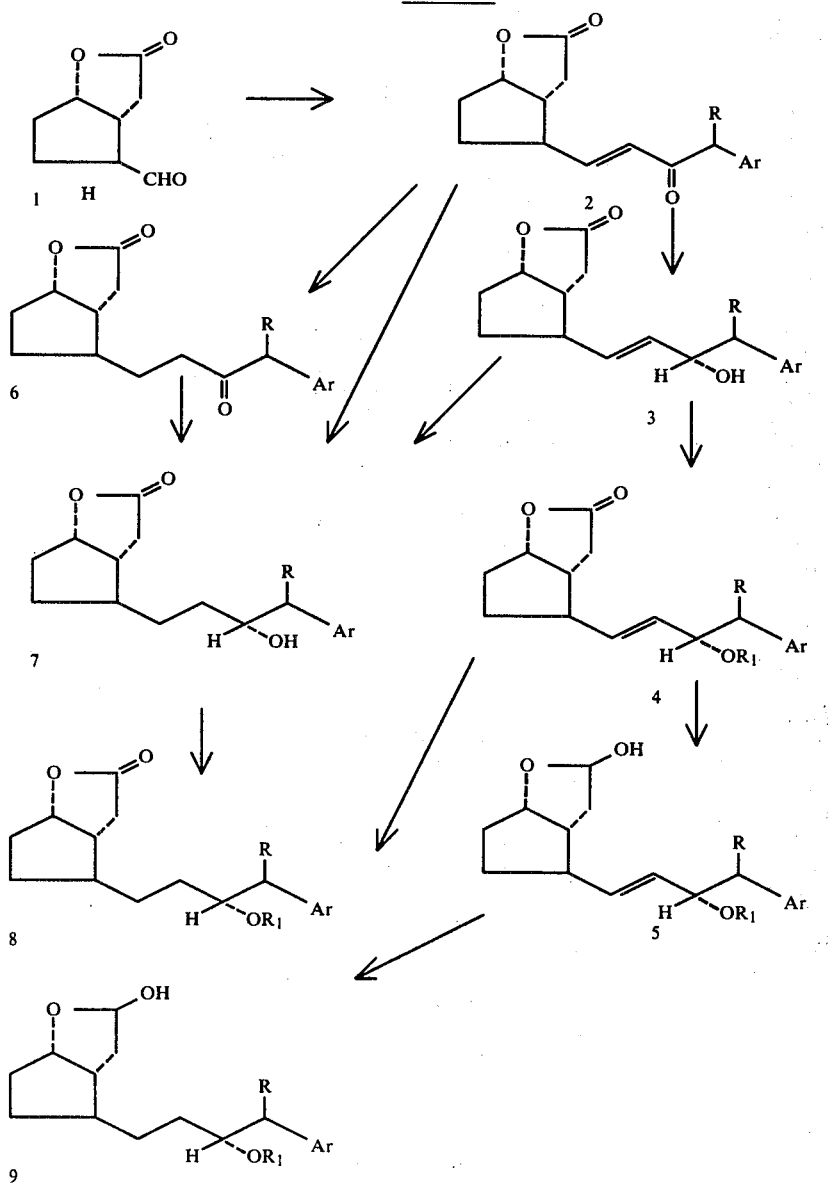

Enone 2 may also be reduced with borohydride ion to produce alcohol 7 in a single step or alternatively, enol 3 may be catalytically reduced to produce alcohol 7 using conditions described above.

(3→4) involves the protection of the free hydroxyl group with an acid labile protecting group. Any sufficiently acid labile group is satisfactory, however, the most usual ones are tetrahydropyranyl or dimethyl-tert-butylsilyl which can be incorporated in molecule by treatment with dihydropyran and an acid catalyst, usually p-toluenesulfonic acid, in an anhydrous medium or dimethyl-tert-butylsilyl chloride and imidazole, respectively.

(4→5) is a reduction of the lactone 4 to hemiacetal 5 using a suitable reducing agent such as disobutyl aluminum hydride in an inert solvent. Low reaction temperatures are preferred and −60° to −80° C. are usual. However, higher temperatures may be employed if over reduction does not occur. 5 is then purified if desired by column chromatography. As indicated in Scheme A, compounds 4 and 5 may be catalytically reduced to 8 and 9 respectively, by the procedure outlined above.

The conversion of (6→9) follows that already outlined by the conversion of (2→5).

The remainder of the synthesis of the two-series prostaglandin analogs is outlined in Scheme B. (5→10) is a Wittig condensation in which hemiacetal 5 is reacted with 4-(carboxy) butyltriphenylphosphonium (229 bromide in dimethyl sulfoxide in the presence of sodium methylsulfinyl methide. 10 is then purified as above. The conversion of 10→11 is an acid catalyzed hydrolysis of protecting group. Any acid may be used which does not cause destruction of the molecule in the course of the removal of the protecting group, however this is accomplished most often by the use of 65% aqueous acetic acid. Alternatively, the dimethyl-tert-butylsilyl protecting group may be removed by the action of tetraalkylammonium fluoride in a solvent such as tetrahydrofuran. The product is purified as above.

11 is an 11-desoxy-15-substituted-ω-pentanorprostaglandin of the $F_{2\alpha}$ series. The prostaglandin analogs of the $E_2$ series (13) are prepared from intermediate 10 which may be oxidized by any reagent capable of oxidizing hydroxyl groups which does not attack double bonds. However, the Jones reagent is usually preferred. The product is purified as above to produce intermediate 12. Intermediate 12 may be converted into the prostaglandin analogs of the $E_2$ series (13) in the same manner as described for (10→11). Furthermore, intermediate 12 may be reduced with sodium borohydride to a mixture of intermediate 15 and its $C_9$ epimer which are separable by column preparative thin layer, or preparative high pressure liquid chromatography and which can be converted into prostaglandin analogs of the $F_{2\alpha}$ and $F_{2\beta}$ series by the methods given for (10→11). Alternatively, compound 13 may be reduced with sodium borohydride to provide the $F_{2\alpha}$ and $F_{2\beta}$ prostaglandin analogs directly. This epimeric mixture may be separated as described above for 15 to provide pure $PGF_{2\alpha}$ and $PGF_{2\beta}$.

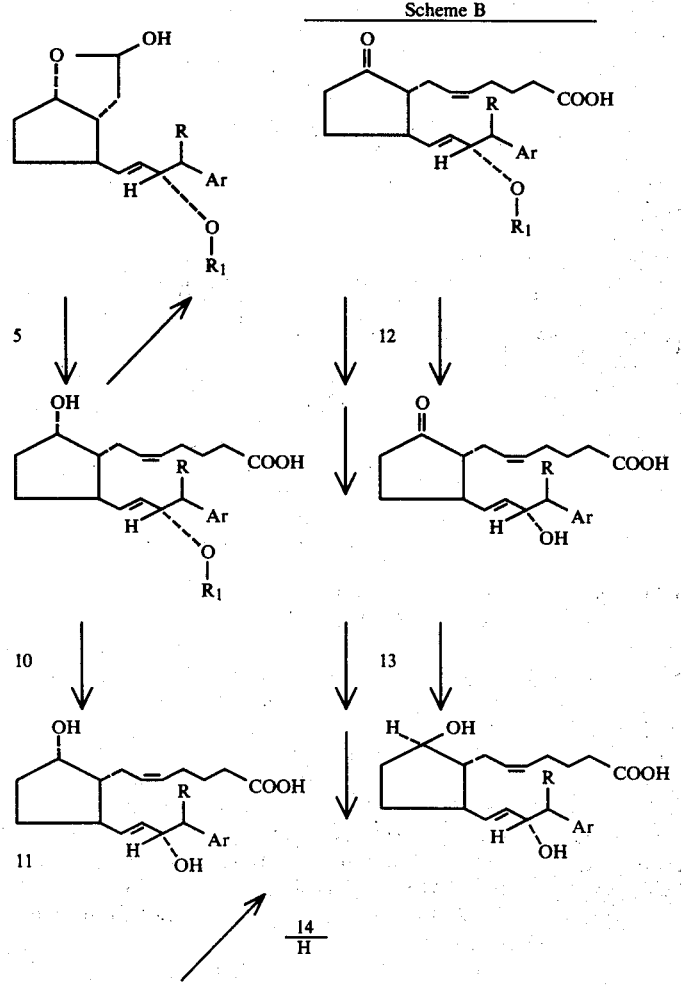

Scheme B

Scheme B

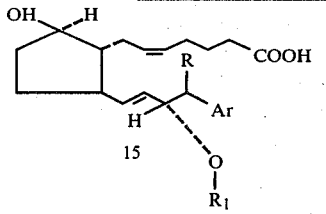

The various reduced prostaglandin analogs, that is prostaglandins of the one series and the zero and 13,14-dihydrotwo series of this invention, are produced as shown on Scheme C. Intermediate 6 may be converted to 19 by the steps already outlined for the conversion of (2→10). 19 may then be converted to 20 by the steps discussed above for the conversion of 10→15. 20 may be catalytically reduced to produce 18 ($R_1$=THP or $(CH_3)_2Si\ C(CH_3)_3$) which is the precursor for the prostaglandin analogs of the zero series of this invention by the steps previously outlined.

(16→17) is a selective catalytic hydrogenation of the 5–6 cis double bond at low temperature using catalysts such as those described above. Especially preferred for this reduction is the use of palladium on carbon as a catalyst and a reaction temperature of $-20°$ C. 17 ($R_1$=THP or $(CH_3)_2Si\ C(CH_3)_3$) is not only a precursor for the prostaglandin analogs of the "one" series but also for the "zero" series since 17 may be reduced to 18 reducing the methods described for (4→8). Similarly, 16 may be reduced to 18 by the same procedure. The removal of the protecting groups is carried out as previously described and 17, 18, 19 and 20 wherein $R_1$=THP or $(CH_3)_2Si\ C(CH_3)_3$ may be deprotected in this way to produce prostaglandins of the "one" series, and the "zero", and 13,14-dihydro-two series of this invention. The production of prostaglandins of the E and F series wherein said prostaglandin is of "zero", "one", or 13,14-dihydro-two series from 16, 17, 18, 19 and 20 follows that previously described for the conversion of 10→11, 12, 13, 14 and 15.

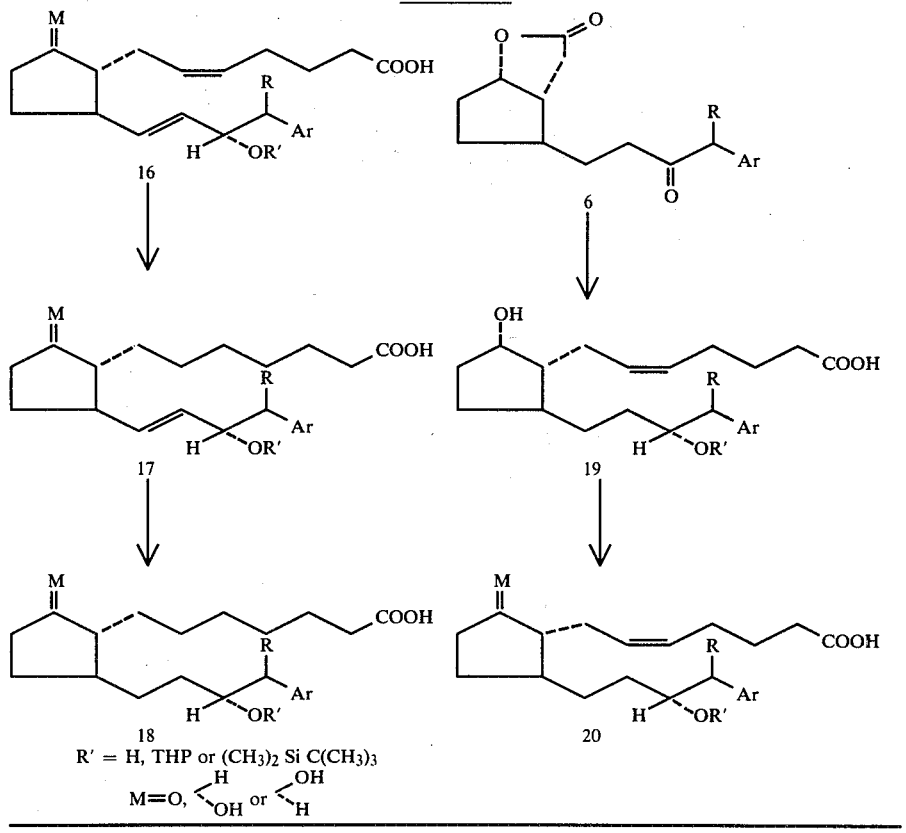

Scheme C $R' = H$, THP or $(CH_3)_2\ Si\ C(CH_3)_3$ $M=O,\ \overset{H}{\underset{OH}{\diagdown}}$ or $\overset{OH}{\underset{H}{\diagdown}}$ Furthermore, the 15-substituted-ω-pentanorprostaglandin analogs of the $E_1$, $F_{1\beta}$ and $F_{1\alpha}$ series may be obtained directly from the corresponding prostaglandin analog of the "2-series", by first protecting the hydroxyl by introducing dimethyl isopropyl silyl groups reducing selectively the cis double bond, and removing the protecting group.

The reduction is usually accomplished as discussed above for 16→17 and removal of the protecting group is accomplished by contacting the reduced protected compound with 3:1 acetic acid: water for 10 minutes or until reaction is substantially complete.

The 11-desoxy-15-substituted-ω-pentanorprostaglandin analogs of the "one" series may be prepared by the alternate synthesis summarized in Scheme D. For the first step in the preparation of the above named prostaglandin analogs, the hemiacetal 2-[5α-hydroxy-2-benzyloxymethylcyclopent-1α-yl]-acetaldehyde, γ-hemiacetal is caused to react with the disodium salt of 4-(carboxy)butyltriphenylphosphonium bromide (22) as described above for 5→10. This intermediate may be converted by procedures described in detail in the appended examples as summarized below.

As shown in Scheme D, hemiacetal 21 is caused to react with the reagent 22 to produce 23.

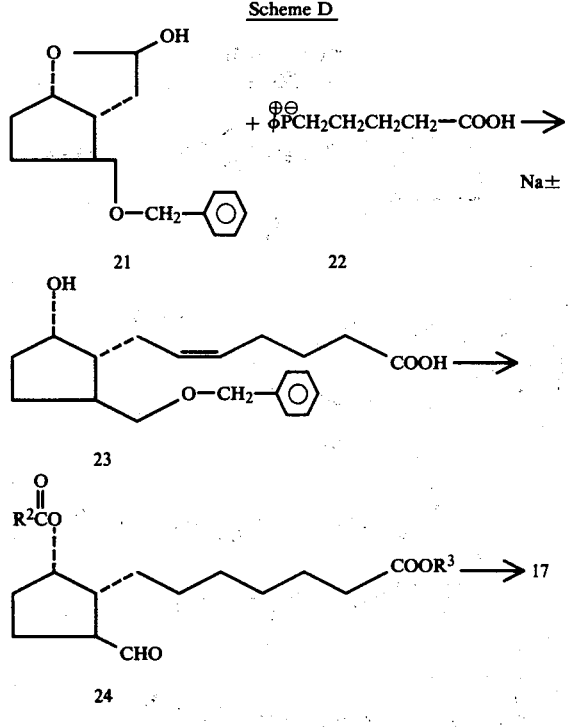

23→24 involves esterifying the carboxyl group with diazomethane to form a methyl ester intermediate. Other blocking groups may be used provided the group is stable to hydrogenation and mild acid hydrolysis and removable by mild basic hydrolysis. Such groups include alkyl of from 1 to 8 carbons, phenalkyl of up to 9 carbons, phenyl, tolyl, p-biphenyl or α- to β-naphthyl. Acylation of the methyl ester intermediate with acetic anhydride and pyridine forms an acetate intermediate. Other blocking groups may be used provided the group is stable to hydrogenation and mild acid hydrolysis. Such groups include alkanoyl of from 2 to 9 carbons, phenalkanoyl of up to 10 carbons, benzoyl, toloyl, p-phenyl benzoyl or α- or β-naphthoyl. The protected benzyl ether upon reduction with hydrogen and palladium on carbon in an appropriate solvent containing a suitable acid catalyst, ethanol and acetic acid or ethyl acetate and hydrochloric acid being especially preferred, affords a hydroxy compound oxidation of which with Collins' reagent yields aldehyde 24.

24→17 involves treatment of 24 with the sodium salt of the appropriate 3-ketophosphonate under conditions described for 1→2, to form an enone reduction of which with a kindred alkyl borohydride such as lithium triethylborohydride or potassium tri-sec-butylborohydride or zinc borohydride forms an enol. The hydroxyl group is then protected by treatment with dihydropyran to form a tetrahydropyranyl ether. Other protecting groups may be employed provided they are stable to mild basic hydrolysis and easily removable by mild acid hydrolysis. Such groups include tetrahydrofuryl, or dimethyl-t-butyl silyl. This protected compound is then contacted with aqueous sodium hydroxide to yield 17. The conversion of 17 to the 11-desoxy-15-substituted-ω-pentanorprostaglandins of the "one" series follows the procedure outlined above.

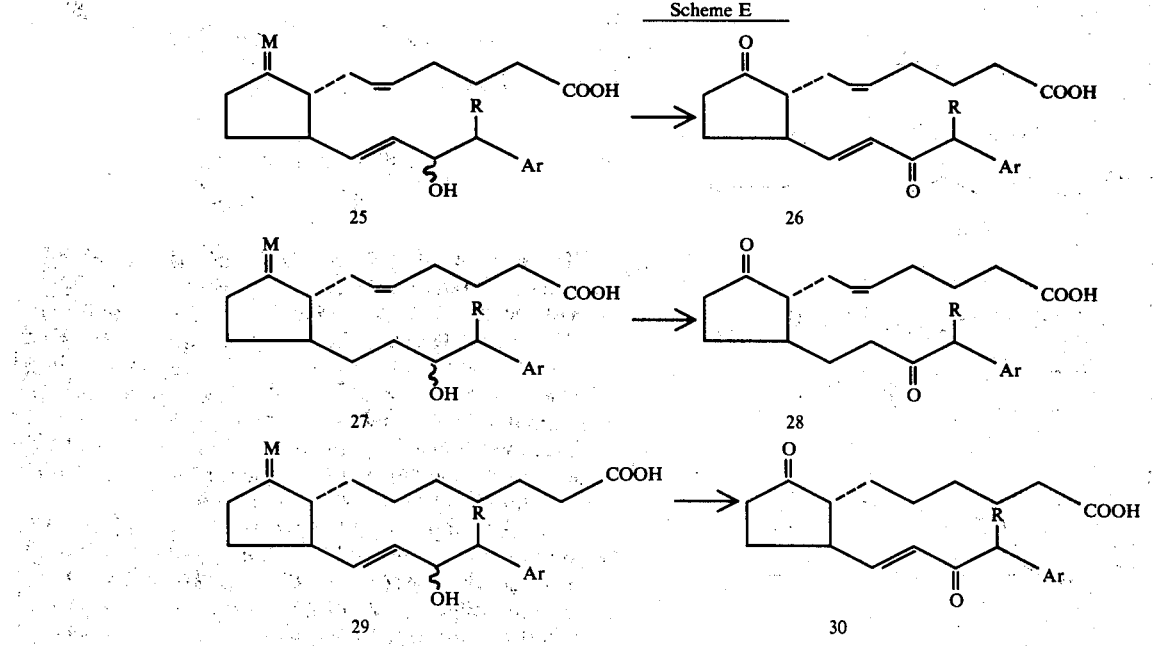

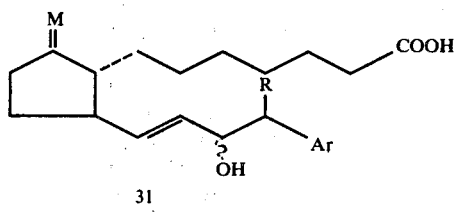
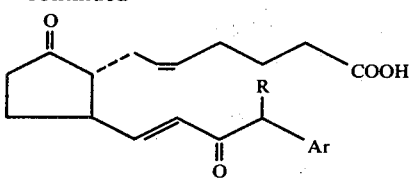

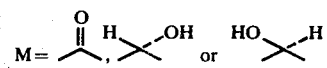

11-desoxy-15-keto-15-substituted-ω-pentanorprostaglandins may be prepared as summarized in Scheme E. 25→26 involves oxidation of the C$_{15}$ alcohol moiety of 25. Any reagent capable of oxidizing hydroxyl groups which does not attack double bonds may be used, however, the Jones' reagent is usually preferred. The 15-keto-prostaglandin E analogs of the 13,14-dihydro-two-, one-, and zero- series may be prepared from compounds 27, 29 and 31 as described for 25→26 above.

Scheme F summarizes the preparation of the 11-desoxy-15-keto-15-substituted-ω-pentanorprostaglandin F$_{2\alpha}$ and F$_{2\beta}$ analogs. 33→34 involves acylation of 33 with acetic anhydride and pyridine to form an acetate intermediate. Other blocking groups may be used provided the group is stable to mild acid hydrolysis. Such groups include alkanoyl of from 2 to 9 carbons, phenalkanoyl of up to 10 carbons, benzoyl, tolyl, p-phenylbenzoyl, or α- or β-naphthoyl. The protecting group at C$_{15}$ is then removed as described above to provide a second intermediate. The next step involves oxidation of the C$_{15}$ alcohol moiety to provide a third intermediate. Any reagent capable of oxidizing hydroxyl groups which does not attack double bonds may be used, however, the Jones' reagent is usually preferred. The last step in this sequence involves transesterification of the protecting group at C$_9$.

Scheme F

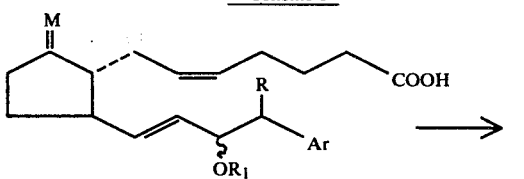

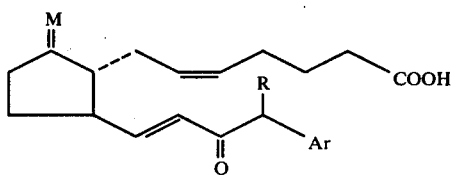

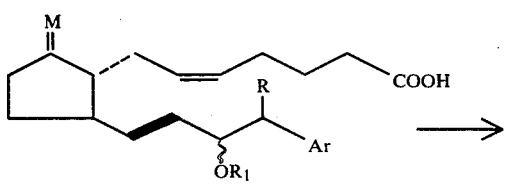

-continued
Scheme F

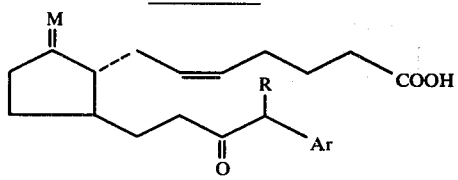

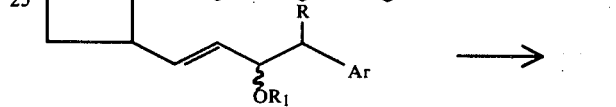

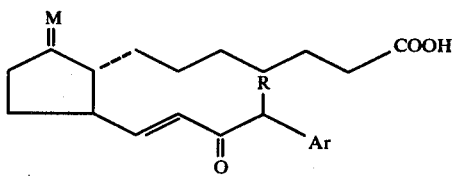

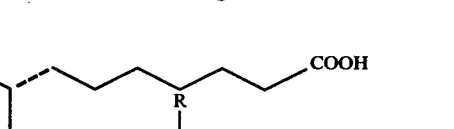

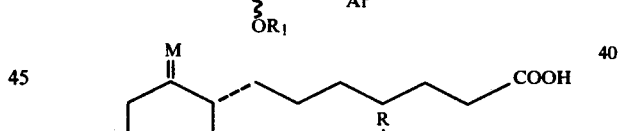

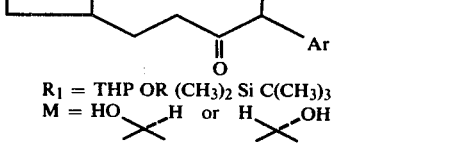

R$_1$ = THP OR (CH$_3$)$_2$ Si C(CH$_3$)$_3$
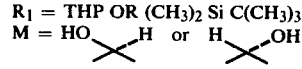

This is usually done by treatment with anhydrous potassium carbonate in an alcoholic solvent such as methanol, which affords the 15-keto F$_{2\alpha}$ or F$_{2\beta}$ analogs. The 15-keto-prostaglandin F$_\alpha$ or F$_\beta$ analogs of the 13,14-dihydro-two-, one-, and zero- series may be prepared from compounds 35, 37 and 39 as described for 33→34.

It should be noted that the stereo-chemistry of the hydroxyl group at C$_{15}$ is unimportant for the preparation of 15-keto compounds; 15β, 15α, or an epimeric mixture will all afford the same 15-keto analog.

In the foregoing procedures, where purification by column chromatography is desired, appropriate chromatographic supports include neutral alumina and silica gel and 60–200 mesh silica gel is generally preferred. The chromatography is suitably conducted in reaction-inert solvents such as ether, ethyl acetate, benzene, chloroform, methylene chloride, cyclohexane and n-hexane, as further illustrated in the appended examples. Where purification by high pressure liquid chromatography is desired, appropriate supports include 'Corasil,' 'Porasil,' and 'Lichrosorb' with inert solvents such as ether, chloroform, methylenechloride, cyclohexane and n-hexane being employed.

In numerous in vivo and in vitro tests we have demonstrated that these prostaglandin analogs possess physiological activities comparable but much more tissue selective and longer acting than those exhibited by the natural prostaglandins (see above). These tests include, among others, a test for effect on isolated smooth muscle from guinea pig uterus, guinea pig ileum and rat uterus, inhibition of histamine-induced bronchospasm in the guinea pig effect, effect on dog blood pressure, inhibition of stress-induced ulceration in the rat, effect on mouse diarrhea, and inhibition of stimulated gastric acid secretion in rats and dogs.

The physiological responses observed in these tests are useful in determining the utility of the test substance for the treatment of various natural and pathological conditions. Such determined utilities include: vasodilator activity, antihypertensive activity, bronchodilator activity, antiarrythmic activity, cardiac stimulant activity, antifertility activity and antiulcer activity.

An advantage possessed by 11-desoxy prostaglandins of the E series in general is their increased stability as compared with such as $PGE_2$. In addition 11-desoxy-15-substituted-$\omega$-pentanorprostaglandins possess highly selective activity profiles compared with the corresponding naturally occurring prostaglandins and, in many cases, exhibit a longer duration of action. These prostaglandin analogs possess useful vasodilator activity. A prime example of the therapeutic importance of the prostaglandin analogs of this invention is the efficacy of 11-desoxy-16-phenyl-$\omega$-tetranorprostaglandin $E_0$ and 15-epi-11-desoxy-16-(m-tolyl)-$\omega$-tetranorprostaglandin $E_2$ which exhibit hypotensive activity of greatly enhanced potency and duration as compared with $PGE_2$ itself and with the corresponding analogs of the $E_1$ and $E_2$ series. At the same time, the smooth muscle stimulating activity is markedly depressed in comparison with $PGE_2$. In a similar manner, other $E_0$ and 13,14-dihydro-$E_2$ analogs of this invention exhibit desirable hypotensive activity.

11-desoxy-16-(m-tolyl)-$\omega$-tetranorprostaglandin $E_2$ and 11-desoxy-16-(5-phenyl-$\alpha$-thienyl)-$\omega$-tetranorprostaglandin $E_2$ exhibit high bronchodilator activity with reduced non-vascular smooth muscle activity. In similar fashion, other 11-desoxy-15-substituted-$\omega$-pentanorprostaglandin $E_1$ and $E_2$ analogs display desirable bronchodilator activity.

Another outstanding example of the therapeutic importance of these prostaglandin analogs is the potent, selective antiulcer and antisecretory activity displayed by the 11-desoxy-16-($\beta$-naphthyl)-$\omega$-tetranor $PGE_2$ and 11-desoxy-15-keto-16-($\beta$-naphthyl)-$\omega$-tetranor $PGE_2$. Similarly, the other PGE and 15-keto analogs possess these desirable gastrointestinal activities.

The $C_1$ phenyl esters of the prostaglandin analogs of this invention are prepared from the corresponding acids by contacting them with the desired phenol in the presence of dicyclohexylcarbodiimide in an inert reaction solvent. The $C_1$ alkyl or phenalkyl esters of the prostaglandin analogs of this invention are prepared from the corresponding acids by contacting them with the appropriate diazo compound in the presence of a reaction inert solvent. Such esters possess the activity of the acid from which they are derived. The esters of the prostaglandin analogs of this invention which are acylated and $C_9$ and/or $C_{15}$ are readily prepared from the corresponding parent by acylation which is usually carried out using carboxylic acid anhydrides or carboxylic acid chloride as the acylation agents. Such acyl groups are lower alkanoyl, benzoyl and substituted benzoyl wherein said substituent is halo, trifluoromethyl, lower alkoxy or phenyl or formyl. Such esters possess the activity of the prostaglandin analog from which they are derived.

The prostaglandin analogs which have a beta hydroxyl at $C_{15}$ and possess a $C_{15}$ lower alkyl group have action which is similar to their epimers. In some cases, however, the selectivity that these compounds display, such as the hypotensive activity of the 15-epi-16-m-tolyl $PGE_2$ analog, exceeds that of the epimeric compounds. Pharmacologically acceptable salts useful for the purposes described above are those with pharmacologically acceptable metal cations, ammonium, amine cations, or quaternary ammonium cations.

Especially preferred metal cations are those derived from the alkali metals. e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, $\alpha$-phenylethylamine, $\beta$-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglucamine, N-methylglucosamine, epherdrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium and the like.

The new compounds of this invention can be used in a variety of pharmaceutical preparations which contain the compound or a pharmaceutically acceptable salt thereof, and they may be administered in the same manner as natural prostaglandins by a variety of routes, such as intravenous, oral and topical, including aerosol, intravaginal, and intranasal, among others.

To produce bronchodilation or to increase nasal potency, an appropriate dosage form would be an aqueous ethanolic solution of 11-desoxy-16-Ar-substituted-$\omega$-tetranor $PGE_1$ or $PGE_2$ employed as an aerosol using fluorinated hydrocarbons as propellant in the amount of from about 3–500 μg/dose.

Whereas the 16-Ar-substituted-ω-tetranorprostaglandin analogs of the $E_2$, $E_0$ and 13,14-dihydro-$E_2$ or $F_\beta$ series are useful hypotensive agents, the optically active 11-desoxy-16-Ar-substituted-ω-tetranorprostaglandins of the $E_0$ series of the formula

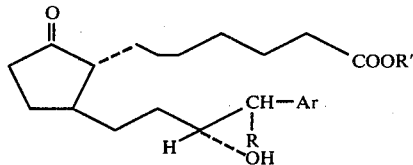

and of the 13,14-dihydro-$E_2$ series of the formula

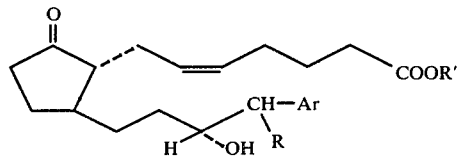

wherein Ar, R and R' are as previously defined, of the present invention have unexpectedly greater potency or duration of effect than the corresponding $E_1$ and $E_2$ analogs. For example, 11-desoxy-16-phenyl-ω-tetranorprostaglandin $E_0$ is about an order of magnitude more potent than the corresponding $E_2$ analog and has a markedly longer duration of effect. Similarly, 11-desoxy-13,14-dihydro-16-phenyl-ω-tetranorprostaglandin $E_2$ is about two orders of magnitude more potent than the $E_2$ analog. Certain 15-epi-11-desoxy-16-Ar-substituted-ω-tetranorprostaglandins of the $E_2$ series, such as 15-epi-11-desoxy-16-(m-tolyl)-ω-tetranorprostaglandin $E_2$, have also been found to show significantly greater potency or duration of effect as hypotensive agents than the 15α-epimer of the corresponding $E_2$ analog. For treatment of hypertension these drugs could appropriately be administered as an intravenous injection at doses of about 0.5–10 μg/kg or preferably in the form of capsules or tablets at doses of 0.005 to 0.5 mg/kg/day.

The 15-keto-16-Ar-substituted-ω-tetranorprostaglandin analogs or 16-Ar substituted-ω-tetranorprostaglandin E analogs are useful antiulcer agents. For treatment of peptic ulcers these drugs may be administered in the form of capsules or tablets at doses of 0.005 to 0.5 mg/kg/day.

To prepare any of the above dosage forms or any of the numerous other forms possible, various reaction-inert diluents, excipients or carriers may be employed. Such substances include, for example, water, ethanol, gelatins, lactose, starches, magnesium stearate, talc, vegetable oils, benzyl alcohols, gums, polyalkylene glycols, petroleum jelly, cholesterol and other known carriers for medicaments. If desired, these pharmaceutical compositions may contain auxiliary substances such as preserving agents, wetting agents, stabilizing agents, or other therapeutic agents such as antibiotics.

The following examples are merely illustrative, and in no way limit the scope of the appended claims. In these examples it will be appreciated that all temperatures are expressed in Centigrade, all melting and boiling points are uncorrected.

EXAMPLE I

2-[2β-Benzyloxymethyl-5α-hydroxycyclopent-1α-yl]acetaldehyde, α-hemiacetal (21):

To a stirred solution, cooled to −78°, of 10.0 g (40.5 mmoles) of 2-[2β-benzyloxymethyl-5α-hydroxycyclopent-1α-yl]acetic acid α-lactone in 100 ml of toluene was added dropwise 55.5 ml of a 20% solution of diisobutylaluminum hydride in hexane. The solution was stirred in the cold under nitrogen for 40 minutes then was quenched by the dropwise addition of methanol until gas evolution ceased. The quenched mixture was warmed to room temperature, then was concentrated. The resultant oil was slurried with hot methanol, filtered, and the filtrate was concentrated. Purification of the crude product by silica oil chromatography using mixtures of benzene:ethyl acetate as eluents provided the colorless, oily 2-[2β-benzyloxymethyl-5α-hydroxycyclopent-1α-yl]acetaldehyde, γ-hemiacetal (21) weighing 8.91 g (86% yield).

EXAMPLE II

7-[2β-Benzyloxymethyl-5α-hydroxycyclopent-1α-yl]-cis-5-heptenoic acid (23):

To a solution of 4.96 g (11.2 mmoles) of 4-carbohydroxy-n-butyl)triphenylphosphonium bromide (22) in 8.85 ml of dimethyl sulfoxide is added dropwise 9.73 ml (21.2 mmoles) of a 2.18 M solution of sodium methylsulfinylmethide in dimethyl sulfoxide. To the resultant red ylide solution is added a solution of 1.12 g (4.50 mmoles) of 2-[2β-benzyloxymethyl-5α-hydroxycyclopent-1α-yl]acetaldehyde, α-hemiacetal (2) in 11 ml of dimethyl sulfoxide. After being stirred for an additional 45 minutes the reaction is poured onto ice-water. The basic aqueous solution is extracted with a 2:1 mixture of ethyl acetate: ether is then covered with ethyl acetate, and is acidified with 1.0 N hydrochloric acid to pH∼3. The aqueous layer is extracted further with ethyl acetate; the combined ethyl acetate extracts are washed with water, are dried (anhydrous magnesium sulfate), and are concentrated. Purification of the crude product by silica gel chromatography affords the desired 7-[2β-benzyloxymethyl-5α-hydroxycyclopent-1a-yl]-cis-5-heptenoic acid (23).

EXAMPLE III

Methyl 7-[2β-benzyloxymethyl-5α-hydroxycyclopent-1α-yl]-cis-5-heptenoate.

A solution of 1.41 g (4.06 mmoles) of 7-[2β-benzyloxymethyl-5α-hydroxycyclopent-1α-yl]-cis-5-heptenoic acid (23) in 17.5 ml of anhydrous ether is titrated at room temperature with an ethereal diazomethane solution until the yellow color persisted for 5 minutes. The reaction is then decolorized by the dropwise addition of glacial acetic acid. The ethereal solution is then washed with saturated sodium bicarbonate and saturated brine, is dried (anhydrous magnesium sulfate), and is concentrated to afford the desired methyl 7-[2β-benzyloxymethyl-5α-hydroxy-cyclopentan-1α-yl]-cis-5-heptenoate.

EXAMPLE IV

Methyl 7-[2β-benzyloxymethyl-5α-acetoxycyclopent-1α-yl]-cis-5-heptenoate.

A mixture of 1.28 g (3.54 mmoles) of methyl 7-[2β-benzyloxymethyl-5α-hydroxycyclopent-1α-yl]-cis-5-heptenoate prepared in Example III, 5.0 ml of pyridine, and 0.736 ml (7.78 mmoles) of acetic anhydride is stirred under nitrogen at 50° overnight. The mixture is then cooled to room temperature and diluted with ether (75 ml). The ethereal solution is washed with water (1x) and with saturated copper (II) sulfate (3x), is dried (anhydrous magnesium sulfate), and concentrated to afford the desired methyl 7-[2β-benzyloxymethyl-5α-acetoxycyclopent-1α-yl]-cis-5-heptenoate.

EXAMPLE V

Methyl 7-[2β-hydroxymethyl-5α-acetoxycyclopent-1α-yl]heptenoate.

A heterogeneous mixture of 1.27 g (3.14 mmoles) of methyl 7-[2β-benzyloxymethyl-5α-acetoxycyclopent-1α-yl]-cis-5-heptenoate prepared in Example IV, 305 mg of 10% palladium on carbon, and 13 ml of a 20:1 mixture of absolute ethanol: glacial acetic acid is stirred at room temperature under one atmosphere of hydrogen for 20 hours. The mixture is then filtered through Celite 545 and the filtrate is concentrated to afford the desired methyl 7-[2β-hydroxymethyl-5α-acetoxycyclopental-1α-yl]heptenoate.

EXAMPLE VI

Methyl 7-[2β-formyl-5α-acetoxycyclopent-1α-yl]heptanoate (24).

To a mechanically stirred solution of 3.37 ml (41.7 mmoles) of pyridine in 50 ml of methylene chloride cooled to 10° to 15° under nitrogen is added portionwise over a period of 30 minutes 1.89 g (18.9 mmoles) of chromium trioxide. The dark burgundy solution was then let warm to room temperature then is cooled to 0°. To the cold solution is added a solution of 747 mg (2.37 mmole) of methyl 7-[2β-hydroxymethyl-5α-acetoxycyclopent-1α-yl] heptanoate prepared in Example V in 7.0 ml of methylene chloride with the concomitant formation of a dense black precipitate. The suspension is stirred in the cold for 15 minutes then 7.21 g (52.2 mmoles) of finely ground sodium bisulfate monohydrate is added. After being stirred for 10 minutes 6.25 g (52.2 mmoles) of anhydrous magnesium sulfate is added. After being stirred for 5 minutes the dark suspension is filtered through a pad of Celite, is washed with methylene chloride, then concentrated by rotary evaporation to afford the crude, methyl 7-[2β-formyl-5α-acetoxycyclopent-1α-yl]heptanoate (24) which is used without purification.

EXAMPLE VII

Methyl 9α-acetoxy-15-oxo-16-(p-chlorophenyl)-13-trans-ω-tetranor prostenoate.

To a suspension of 110 mg (2.61 mmoles) of a 57.0% dispersion of sodium hydride in mineral oil in 20 ml of tetrahydrofuran is added 740 mg (2.61 mmoles) of dimethyl-2-oxo-3-(p-chlorophenyl) propyl phosphonate. The mixture is then stirred at room temperature for 1 hour under nitrogen. To this mixture is added a solution of 744 mg (2.37 mmoles) of the crude methyl 7-[2β-formyl-5α-acetoxycyclopent-1α-yl]heptenoate (24) in 4 ml of tetrahydrofuran. The resultant reaction mixture is stirred at room temperature for 2.0 hours under nitrogen. The reaction is then quenched by the addition of glacial acid to pH~7 and is concentrated by rotary evaporation. The crude product is purified by chromatography on silica gel to provide the desired methyl 9α-acetoxy-15-oxo-16-(p-chlorophenyl)-13-trans-ω-tetranorprostenoate.

EXAMPLE VIII

Methyl 9α-acetoxy-15α-hydroxy-16-(p-chlorophenyl)-13-trans-ω-tetranorprostenoate and methyl 9α-acetoxy-15β-hydroxy-16-(p-chlorophenyl)-13-trans-ω-tetranorprostenoate.

To a solution, cooled under nitrogen to −78°, of 900 mg (2.0 mmoles) of methyl 9α-acetoxy-15-oxo-16-(p-chlorophenyl)-13-trans-ω-tetranorprostenoate prepared in Example VII in 30 ml of tetrahydrofuran is added 2.0 ml of a 1.0 m solution of lithium triethylborohydride in tetrahydrofuran. The reaction mixture is stirred in the cold for 30 minutes then is quenched by the addition of 1 ml of a 9:1 mixture of water:acetic acid. The quenched reaction mixture is let warm to room temperature, then is concentrated. The resultant product is diluted with ethyl acetate; the organic layer is extracted with water and saturated sodium bicarbonate, is dried (anhydrous magnesium sulfate), and is concentrated. Purification of the resultant product by silica gel chromatography affords the methyl 9α-acetoxy-15β-hydroxy-16-(p-chlorophenyl)-13-trans-ω-tetranorprostenoate and the methyl 9α-acetoxy-15α-hydroxy-16-(p-chlorophenyl)-13-trans-ω-tetranorprostenoate. The 15β product of this example may be converted into the 15-epi-11-desoxy-16-p-chlorophenyl-ω-tetranorprostaglandin $E_1$, $F_{1\alpha}$, and $F_{1\beta}$ compound by the procedures of examples IX-–XII, XXIII, and XXVI.

EXAMPLE IX

9α,15α-Dihydroxy-16-(p-chlorophenyl)-13-trans-ω-tetranorprostenoic acid (17a).

A mixture of 100 mg of methyl 9α-acetoxy-15α-hydroxy-16-(p-chlorophenyl)-13-trans-ω-tetranorprostenoate prepared in Example VIII, 1.0 ml of 1.0 N aqueous sodium hydroxide, 1.0 ml of tetrahydrofuran, and 1.0 ml of absolute methanol is stirred under nitrogen at room temperature for 1.5 hours. The solution is then acidified by the addition of 1.0 ml of 1.0 N aqueous hydrochloric acid (pH of acidified solution was ca. 5). The acidified solution is then extracted with ethyl acetate. The combined extracts are dried (anhydrous magnesium sulate) and concentrated. Purification of the crude product provides the 9α, 15α-dihydroxy-16-(p-chlorophenyl)-13-trans-ω-tetranorprostenoic acid (17a).

EXAMPLE X

Methyl 9α-acetoxy-15α-(tetrahydropyran-2-yloxy)-16-(p-chlorophenyl)-13-trans-ω-tetranorprostenoate.

A mixture of 453 mg (1.0 mmole) of the methyl 9α-acetoxy-15α-hydroxy-16-(p-chlorophenyl)-13-trans-ω-tetranorprostenoate prepared in Example VIII, 0.14 ml (1.53 mmoles) of dihydropyran, 4.2 ml of methylene chloride, and 1 crystal of p-toluenesulfonic acid monohydrate is stirred at room temperature under nitrogen for 20 minutes. The reaction mixture is then diluted with ether, washed with saturated aqueous sodium bicarbonate, dried (anhydrous magnesium sulfate), and concentrated to give the methyl 9α-acetoxy-15α-(tetrahydropyran-2-yloxy)-16-(p-chlorophenyl)-trans-13-ω-tetranorprostenoate.

EXAMPLE XI

9α-hydroxy-15α-(tetrahydropyran-2-yloxy)-16-(p-chlorophenyl)-13-trans-ω-tetranorprostenoic acid (17a).

A homogeneous solution of 537 mg (1.0 mmole) of methyl 9α-acetoxy-15α-(tetrahydropyran-2-yloxy)-16-(p-chlorophenyl)-13-trans-ω-tetranorprostenoate prepared in Example X 3.0 ml (3.0 mmoles) of a 1.0 N aqueous sodium hydroxide solution, 3.0 ml of methanol, and 3.0 ml of tetrahydrofuran is stirred under nitrogen overnight. The reaction is then quenched by the addition of 3.0 ml (3.0 mmoles) of a 1.0 N aqueous hydrochloric acid solution. The quenched solution is diluted with ethyl acetate. The organic layer is dried (anhydrous magnesium sulfate) and concentrated. The crude product is purified by silica gel chromatography to afford the desired 9α-hydroxy-15α-(tetrahydropyran-2-yloxy)-16-(p-chlorophenyl)-13-trans-ω-tetranorprostenoic acid (17a).

EXAMPLE XII 9-oxo-15α-(tetrahydropyran-2-yloxy)-16-(p-chlorophenyl)-13-trans-ω-tetranorprostenoic acid (17a).

To a solution, cooled under nitrogen to −15° to −20°, of 199 mg (0.371 mmole) of 9α-hydroxy-15α-(tetrahydropyran-2-yloxy)-16-(p-chlorophenyl)-13-trans-ω-tetranorprostenoic acid (17a) in 4.0 ml of acetone is added dropwise 0.163 ml (0.408 mmole) of Jones' reagent. The reaction is stirred in the cold for 15 minutes then is quenched by the addition of 0.194 ml of isopropanol. The quenched reaction is stirred in the colf for 5 minutes then is diluted with ethyl acetate. The organic solution is washed with water and saturated brine, dried (anhydrous magnesium sulfate), and concentrated to afford the 9-oxo-15α-(tetrahydropyran-2-yloxy)-16-(p-chlorophenyl)-13-trans-ω-tetranorprostenoic acid (17a) which is used without purification.

EXAMPLE XIII 9-oxo-15α-hydroxy-16-(p-chlorophenyl)-13-trans-ω-tetranorprostenoic acid (17a).

A homogeneous solution of 175 mg (0.328 mmole) of the 9-oxo-15α-(tetrahydropyran-2-yloxy)-16-(p-chlorophenyl)-13-trans-ω-tetranorprostenoic acid (17a) in 5 ml of a 65:35 mixture of acetic acid:water is stirred under nitrogen for 20 hours. The reaction is concentrated by rotary evaporation followed by oil pump. The crude product is purified by silica gel chromatography to provide the 9-oxo-15α-hydroxy-16-(p-chlorophenyl)-13-trans-ω-tetranorprostenoic acid (17a). The product of this example (17a) may be reduced as described in Example XXIII to provide the corresponding PGF$_{2\alpha}$ and PGF$_{2\beta}$ analogs.

EXAMPLE XIV

Dimethyl 2-oxo-3-phenylpropylphosphonate.

A solution of 6.2 g (50 mmoles) dimethyl methylphosphonate (Aldrich) in 125 ml dry tetrahydrofuran was cooled to −78° in a dry nitrogen atmosphere. To the stirred phosphonate solution was added 21 ml of 2.37 M n-butyllithium in hexane solution (Alfa Inorganics, Inc.) dropwise over a period of 18 minutes at such a rate that the reaction temperature never rose above −65°. After an additional 5 minutes stirring at −78°, 7.5 g (50.0 mmole) methyl phenylacetate was added dropwise at a rate that kept the reaction temperature less than −70° (20 minutes). After 3.5 hours at −78° the reaction mixture was allowed to warm to ambient temperature, neutralized with 6 ml acetic acid and rotary evaporated to a white gel. The gelatonous material was taken up in 75 ml water, the aqueous phase extracted with 100 ml portions of chloroform (3x), the combined organic extracts were backwashed (50 cc H$_2$O), dried (MgSO$_4$), and concentrated (water aspirator) to a crude residue and distilled, b.p. 134°-5° (<0.1 mm) to give 3.5 g (29%) dimethyl 2-oxo-3-phenylpropylphosphonate. (2).

The nmr spectrum (CDCl$_3$) showed a doublet centered at 37.δ (J=11.5 cps, 6H) for

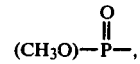

a triplet centered at 3.37δ (2H) for CH$_3$—O—CH$_2$—CH$_2$—, a singlet at 3.28δ (3H) for CH$_3$—O—CH$_2$—, a doublet centered at 3.14 δ (J=23 cps, 2H)

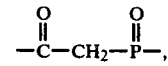

a singlet at 3.9δ (2H) for

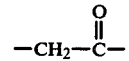

and a broad singlet at 7.2δ (6H) for C$_6$H$_5$—.

EXAMPLE XV (nat.)-2-[5α-Hydroxy-2β-(3-oxo-4-phenyl-trans-1-buten-1yl)cyclopent-1α-yl]acetic acid, γ-lactone (2b):

Dimethyl 2-oxo-3-phenylpropylphosphonate (6.93 g, 28.6 mmole) in 420 ml anhydrous THF was treated with 1.21 g (28.6 mmole) 57% sodium hydride in a dry nitrogen atmosphere at room temperature. After 60 min. of stirring, 2-[5α-hydroxy-2β-formylcyclopentan-1α-yl]acetic acid, γ-lactone (1) in 50 ml anhydrous THF was added. After 95 minutes the reaction mixture was quenched with 4.2 ml glacial acetic acid, filtered, evaporated and combined with 250 ml ethyl acetate which was washed successively with 100 ml saturated sodium bicarbonate solution (2x), 150 ml water (1x), 150 ml saturated brine (1x), dried (Na$_2$SO$_4$) and evaporated to yield 2.51 g (nat)-2-[5α-hydroxy-2β-(3-oxo-4-phenyl-trans-1-buten-1yl)cyclopent-1α-yl]acetic acid, γ-lactone (2b) as a solid after column chromatography (Silica gel, Baker 60-200 mesh), m.p. 52°-56°, [α]$_D^{25}$= +35.0° (C=0.8, CHCL$_3$).

The nmr spectrum (CDCl$_3$) exhibited a doublet of doublets centered at 6.80δ (1H, J=7, 16 cps) and a doublet centered at 6.27δ (1H, J=16 cps) for the olefinic protons, a broad singlet at 7.26δ (5H) for

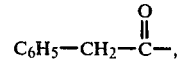

a singlet at 3.82δ (2H) for C₆H₅

and multiplets at 4.78–5.18δ (1H) and 1.2–2.8δ (8H) for the remainder of the protons.

EXAMPLE XVI (nat.) 2-[5α-hydroxy-2β-(3α-hydroxy-4-phenyl-trans-1-buten-1-yl)cyclopent-1α-yl]acetic acid, γ-lactone (3b).

To a solution of 2.5 g (9.25 mmoles) (nat.) 2-[5α-hydroxy-2β-(3-oxo-4-phenyl-trans-1-buten-1-yl)cyclopent-1α-yl]acetic acid, γ-lactone (3) in 30 ml dry THF in a dry nitrogen atmosphere at −78° was added dropwise 9.25 ml of a 1.0 M lithium triethylborohydride solution. After stirring at −78° for 30 min, 20 ml of acetic acid/water (40:60) was added. After the reaction came to room temperature, 40 ml of water was added and the reaction was extracted with methylene chloride (3×50 ml), washed with brine (2×5 ml), dried (Na₂SO₄) and concentrated (water aspirator). The resultant oil was purified by column chromatography on silica gel (Baker "Analyzed" Reagent 60–200 mesh) using cyclohexane and ether as eluents. After elution of less polar impurities a fraction containing 365 mg (nat.) 2-[5α-hydroxy-2β-(3α-hydroxy-4-phenyl-trans-1-buten-1yl)cyclopent-1α-yl]acetic acid, γ-lactone (3b), a 578 mg fraction of mixed 3b and epi-3b and finally a fraction (489 mg) of (nat.) 2-[5α-hydroxy-2β-(3β-hydroxy-4-phenyl-trans-1-buten-1-yl)cyclopent-1α-yl]acetic acid. γ-lactone (epi-3b) were obtained.

The (nat.) 3b had $[\alpha]_D^{25} = +6.623°$ (C 1.0 CHCl₃) and (nat.) epi-3b had $[\alpha]_D^{25} = +24.305°$ (C=1.69, CHCl₃).

The 15-epi product of this example (epi-3b) can be converted into the 15-epi-11-deshydroxyprostaglandins by the procedures of examples XVII-XXX abd XXXII-XXXV.

The products of this example (3b and epi-3b) may be converted into the 13,14-dihydro-11-desoxyprostaglandin two-series analogs by the procedures of examples XXXII, XVIII-XXI, XXIII, XXVI, XXVII-XXX and XXXIV-XXXV.

EXAMPLE XVII (nat.)-2-[5α-hydroxy-2β-(3α-(tetrahydropyran-2-yloxy)-4-phenyl-trans-1-buten-1-yl)cyclopent-1α-yl]acetic acid, γ-lactone (4b).

To a solution of 805 mg (2.96 mmole) (nat.) 2-[5α-hydroxy-2β-[3α-hydroxy-4-phenyl-trans-1-buten-1-yl]cyclopent-1α-yl]acetic acid, γ-lactone (3b) in 20 ml anhydrous methylene chloride and 0.735 ml of 2,3-dihydropyran at 0° in a dry nitrogen atmosphere was added 35.3 mg p-toluenesulfonic acid, monohydrate. After stirring for 35 minutes, the reaction mixture was combined with 150 ml ether, the ether solution washed with saturated sodium bicarbonate (2×100 ml) then saturated brine (1×100 ml), dried (Na₂SO₄) and concentrated to yield 1.2 g (>100%) crude (nat.) 2-[5α-hydroxy-2β-(3α-tetrahydropyran-2-yloxy)-4-phenyl-trans-1-buten-1-yl)cyclopent-1α-yl]acetic acid, γ-lactone (4b).

The ir (CHCl₃) spectrum had a medium adsorbtion at 975 cm⁻¹ for the trans-double bond and a strong adsorbtion at 1770 cm⁻¹ of the lactone carbonyl.

EXAMPLE XVIII (nat.)-2-[5α-hydroxy-2β-(3α-(tetrahydropyran-2-yloxy)-4-phenyl-trans-1-buten-1-yl)cyclopent-1α-yl]acetaldehyde, γ-hemiacetal (5b).

A solution of 1.1 g (2.96 mmole) 2-[5α-hydroxy-2β-(3α-(tetrahydropyran-2-yloxy)-4-phenyl-trans-1-buten-1-yl)cyclopent-1α-yl]acetic acid, γ-lactone (4b) in 15 ml dry toluene was cooled to −78° in a dry nitrogen atmosphere. To this cooled solution was added 4.05 ml of 20% diisobutylaluminum hydride in n-hexane (Alfa Inorganics) dropwise at such a rate so that the internal temperature never rose above −65° (15 minutes). After an additional 30 minutes of stirring at −78°, anhydrous methanol was added until gas evolution ceased and the reaction mixture was allowed to warm to room temperature. The reaction mixture was combined with 150 ml ether, washed with 50% sodium potassium tartrate solution (2×50 ml), brine (1>75 ml), dried (Na₂SO₄) and concentrated to yield 883 mg (nat.)-2-[5α-hydroxy-2β-(3α-(tetrahydropyran-2-yloxy)-4-phenyl-trans-1-buten-1-yl)cyclopent-1-yl]acetaldehyde, γ-hemiacetal (5b) after column chromatography.

EXAMPLE XIX

9α-hydroxy-15α-(tetrahydropyran-2-yloxy)-16-phenyl-cis-5-trans-13-tetranorprostadienoic acid (10b):

To a solution of 3.83 g (4-carbohydroxy-n-butyl)triphenylphosphonium bromide (23) in a dry nitrogen atmosphere in 10 ml dry dimethyl sulfoxide was added 11.9 ml of a 2.1 M solution of sodium methylsulfinylmethide in dimethyl sulfoxide. To this red ylide solution was added dropwise a solution of 1.2 g (3.3 mmole) 2-[5α-hydroxy-2β-(3α-(tetrahydropyran-2-yloxy)-4-phenyl-trans-1-buten-1-yl)cyclopent-1α-yl]acetaldehyde, γ-hemiacetal (5b) in 15.0 ml dry dimethyl sulfoxide over a period of 20 minutes. After an additional 20 hr stirring at room temperature, the reaction mixture was poured onto ice water, 10% HCl (60 ml), and ethyl acetate (100 ml). The acidic solution was extracted with ethyl acetate (2×100 ml) and the combined organic extracts washed with water (1×100 ml), brine (100 ml), dried (MgSO₄) and evaporated to a residue. The residue was purified by column chromatography on silica gel (Baker "Analyzed" Reagent 60–200 mesh) using chloroform and ethyl acetate as eluents. After removal of high R_f impurities, 2.0 g of 9α-hydroxy-15α-(tetrahydropyran-2yloxy)-16-phenyl-cis-5-trans-13-ω-tetranorprostadienoic acid (10b) was collected.

The product of this example (10b) may be hydrolyzed by the procedure of Example XXI to the 9α,15α-dihydroxy-16-phenyl-cis-5-trans-13-ω-tetranorprostadienoic acid (11b). The product of this example (10b) may also be converted by the procedures of Examples XXIV and XXV into the 9α,15α-dihydroxy-16-phenyl-trans-13-ω-tetranorprostenoic acid (17b), by the procedures of Examples XXII and XXI into the 9α,15α-dihydroxy-16-phenyl--tetranorprostanoic acid (18b), or by the procedures of Examples XXI and XXVI into the 9,15-dioxo-16-phenyl-cis-5-trans-13-ω-tetranorprostadienoic acid (34b).

EXAMPLE XX 9-oxo-15α-(tetrahydropyran-2-yloxy)-16-phenyl-cis-5-trans-13-ω-tetranorprostadienoic acid (12b):

To a solution cooled to −10° under nitrogen of 1.33 g (2.9 mmole) 9α-hydroxy-11-desoxy-15α-(tetrahydropyran-2-yloxy)-16-phenyl-5-trans-13-ω-tetranorprostadienoic acid (10b) in 30 ml reagent grade acetone was added dropwise to 1.26 ml of Jones' reagent. After 5 minutes at −10° 1.0 ml 2-propanol was added and the reaction mixture was allowed to stir an additional 5 minutes at which time it was combined with 100 ml ethyl acetate, washed with water (3×50 ml), brine (1×50 ml), dried (MgSO$_4$) and concentrated to give 1.3 g of 9-oxo-15α-(tetrahydropyran-2-yloxy)-16-phenyl-cis-5-trans-13-ω-tetranorprostadienoic acid (12b)

The product of this example (12b) may be converted by the procedures of Examples XXIII and XXI into the corresponding 11-desoxy-prostaglandin F$_{2α}$ and F$_{2β}$ analogs. The product of this example (12b) may also be converted by the procedures of Examples XXII and XXI into the 9-oxo-15α-hydroxy-16-phenyl-ω-tetranorprostanoic acid (18b).

EXAMPLE XXI 9-oxo-15α-hydroxy-16-phenyl-cis-5-trans-13-ω-tetranorprostadienoic acid (13b):

A solution of 1.3 g 9-oxo-15α-(tetrahydropyran-2-yloxy)-16-phenyl-cis-5-trans-13-prostadienoic acid (12b) in 20 ml of a 65:35 mixture of glacial acetic acid:water was stirred under nitrogen at 25° for 18 hours then was concentrated by rotary evaporation. The resultant crude oil was purified by column chromatography on silica gel (Mallinckrodt CC-7) using chloroform and ethyl acetate as eluents. After elution of less polar impurities the desired 9-oxo-15α-hydroxy-16-phenyl-cis-5-trans-13-ω-tetranorprostadienoic acid (13b) weighing 450 mg was collected. The ir spectrum (CHCl$_3$) exhibited a broad hydroxyl absorption (3200–3650 cm$^{-1}$), strong carbonyl absorptions at 1740 cm$^{-1}$ (ketone) and 1710 cm$^{-1}$ (acid) and a medium absorption at 970 cm$^{-1}$ for the trans double bond.

EXAMPLE XXII 9-oxo-11-desoxy-15α-hydroxy-16-phenyl-ω-tetranorprostanoic acid (18b).

A heterogenous mixture of 800 mg of 9-oxo-11-desoxy-15α-hydroxy-16-phenyl-cis-5-trans-13-ω-tetranorprostanoic acid (13b) and 100 mg of 10% palladium on carbon in 50 ml of methanol is stirred under 1 atmosphere of hydrogen for 2.0 hours. The mixture is then filtered through a pad of Celite and the filtrate concentrated. Purification of the crude product by silica gel chromatography using chloroform as eluent provides the desired 9-oxo-11-desoxy-15α-hydroxy-16-phenyl-ω-tetranorprostanoic acid (18b).

EXAMPLE XXIII

9α,15α-dihydroxy-16-phenyl-ω-tetranorprostanoic acid (18b) and
9β,15α-dihydroxy-16-phenyl-ω-tetranorprostanoic acid (18b).

To a solution of 100 mg of 9-oxo-15α-hydroxy-16-phenyl-ω-tetranorprostanoic acid (18b) in 30 ml of methanol, cooled to 0°, was added a solution of 500 mg of sodium borohydride in 50 ml of methanol cooled to 0°. The reaction was let stir at 0° for 20 minutes then for 1.0 hour at room temperature. The reaction was then diluted with 6 ml of water and was concentrated. The concentrated solution was overlaid with ethyl acetate then acidified to pH 3 with 10% hydrochloric acid. The ethyl acetate layer was washed with water (2×10 ml) and saturated brine (10 ml), was dried (sodim sulfate) and was concentrated. The crude residue was purified by silica gel column chromatography using mixtures of chloroform: methanol as eluents to provide first 9α,15α-dihydroxy-16-phenyl-ω-tetranorprostanoic acid (18b) as a viscous oil weighing 16 mg, 58 mg of a mixture of C$_9$ epimers, and finally 9β,15α-dihydroxy-16-phenyl-ω-tetranorprostanoic acid (18b) as a viscous oil weighing 10 mg.

EXAMPLE XXIV 9-oxo-15β-(tetrahydropyran-2-yloxy)-16-(m-tolyl)-13-trans-ω-tetranorprostenoic acid (17c).

A solution of 200 mg (0.445 mmole) 9-oxo-15β-(tetrahydropyran-2-yloxy)-16-(m-tolyl)-5-cis, 13-trans prostadienoic acid (16c) in 20 ml ethyl acetate containing 30 mg 10% Pd/C was stirred in 1 atm hydrogen at 0°–5° for one hour. At this time hydrogen uptake had stopped. The mixture was filtered and evaporated affording 200 mg 9-oxo-15β-(tetrahydropyran-2-yloxy)-16-(m-tolyl)-13-trans-ω-tetranorprostenoic acid (17c) as a colorless oil.

EXAMPLE XXV 9-oxo-15β-hydroxy-16-(m-tolyl)-13-trans-ω-tetranorprostenoic acid (17c).

A solution of 200 mg (0.445 mmole) 9-oxo-15β-(tetrahydropyran-2-yloxy)-16-(m-tolyl)-13-trans-ω-tetranorprostenoic acid (17c) in 10 ml of a 65:35 mixture of glacial acetic acid:water was stirred under nitrogen at 25° for 18 hours then concentrated by rotary evaporation. The resultant crude oil was purified by column chromatography on silica gel (Mallinckrodt CC-7) using methylene chloride and ether as eluents. After elution of less polar impurities the desired 9-oxo-15β-hydroxy-16-(m-tolyl)-13-trans-ω-tetranorprostenoic acid (17c) weighing 50 mg was collected. The ir spectrum (CHCl$_3$) exhibited a broad hydroxyl absorbtion at (3650–3200 cm$^{-1}$), strong carbonyl absorbtion at 1740 cm$^{-1}$ and 1710 cm$^{-1}$ for the ketone and acid respectively and absorbtion at 970 cm$^{-1}$ for the trans double bond.

EXAMPLE XXVI 9,15-dioxo-16-(m-tolyl)-5-cis, 13-trans-ω-tetranorprostadienoic acid (26c).

To a solution, cooled to −10° under nitrogen, of 130 mg (0.35 mmole) 9-oxo-15α-hydroxy-16-(m-tolyl)-5-cis, 13-trans-ω-tetranorprostadienoic acid (25c) in 20 ml reagent grade acetone was added 0.14 Jones' reagent. After 3 minutes at 0°, 5 drops of 2-propanol were added and the reaction mixture allowed to stir an additional 5 minutes at which time it was diluted with 50 ml ethyl acetate, washed with water (2×20 ml), brine (1×20 ml), dried (Na$_2$SO$_4$) and concentrated by rotary evaporation. The resultant crude oil was purified by column chromatography on silica gel (Brinkman). After elution of less polar impurities, the desired 9,15-dioxo-16-(m-tolyl)-5-cis, 13-trans-ω-tetranorprostadienoic acid (26c) weighing 100 mg was collected. The ir spectrum (CHCl$_3$), exhibited strong carbonyl absorbtion at 1740 cm$^{-1}$ for the ketone, 1710 cm$^{-1}$ for the acid and at 1660 cm$^{-1}$ and 1610 cm$^{-1}$ for the enone.

EXAMPLE XXVII

9α-acetoxy-15α-(tetrahydropyran-2-yloxy)-16-(m-tolyl)-5-cis, 13-trans-ω-tetranorprostadienoic acid:

A mixture of 300 mg (0.625 mmole) 9α-hydroxy-15α-(tetrahydropyran-2-yloxy)-16-(m-tolyl)-5-cis, 13-trans-ω-tetranorprostadienoic acid (33c), 1.88 ml pyridine and 0.28 ml acetic anhydride was stirred under N$_2$ at 50° for 5 hrs then poured onto ice-water and extracted with ethyl acetate. The ethyl acetate extracts were washed with water (1 × 20 ml), and brine (1 × 20 ml), dried (Na$_2$SO$_4$) and concentrated to give 306 mg 9α-acetoxy-15α-(tetrahydropyran-2-yloxy)-16-(m-tolyl)-5-cis, 13-trans-ω-tetranorprostadienoic acid.

EXAMPLE XXVIII

9α-acetoxy-15α-hydroxy-16-(m-tolyl)-5-cis-13-trans-ω-tetranorprostadienoic acid.

A solution of 306 mg 9α-acetoxy-15α-(tetrahydropyran-2-yloxy)-16-(m-tolyl)-5-cis-13-trans-ω-tetranorprostadienoic acid in 10 ml of a 65:35 mixture of glacial acetic acid: water was stirred under nitrogen at 25° for 18 hours then concentrated by rotary evaporation The resultant crude oil was purified by column chromatography on silica gel (Baker) using ethyl acetate and methylene chloride as eluents. After elution of less polar impurities, the desired 9α-acetoxy-15α-hydroxy-16-(m-tolyl)-5-cis-13-trans-ω-tetranorprostadienoic acid weighing 85 mg was collected. The ir spectrum (CHCl$_3$) exhibited absorbtion carbonyl absorbtion at 1730 cm$^{-1}$ and broad hydroxyl absorbtion at (3650–3200).

EXAMPLE XXIX

9α-acetoxy-15-oxo-16-(m-tolyl)-5-cis-13-trans-ω-tetranorprostadienoic acid.

To a solution cooled to −10° under N$_2$ of 85 mg (0.19 mmole) 9α-acetoxy-15α-hydroxy-16-(m-tolyl)-5-cis-13-trans-ω-tetranorprostadienoic acid in 10 ml of reagent grade acetone was added 0.07 ml Jones' reagent. After 3 minutes at 0°, 5 drops 2-propanol were added and the reaction mixture allowed to stir an additional 5 minutes at which time it was diluted with 50 ml ethyl acetate, washed with water (2×20 ml), brine (1×20 ml), dried (Na$_2$SO$_4$) and concentrated to give 80 mg 9α-acetoxy-15-oxo-16-(m-tolyl)-5-cis-13-trans-ω-tetranorprostadienoic acid.

EXAMPLE XXX

9α-hydroxy-15-oxo-16-(m-tolyl)-5-cis, 13-trans-ω-tetranorprostadienoic acid (34c).

A mixture of 80 mg (0.18 mmole) 9α-acetoxy-15-oxo-16-(m-tolyl)-5-cis-13-trans-ω-tetranorprostadienoic acid 0.5 ml 1.0 N aqueous sodium hydroxide, 2 ml of tetrahydrofuran and 1.5 ml methanol was stirred at 27° for 12 hrs. The reaction was concentrated by rotary evaporated and the crude product was purified by chromatography on silica gel (Mallincrodt CC-7) eluting with methylene chloride and ethyl acetate. After elution of less polar impurities, the 9α-hydroxy-15-oxo-16-(m-tolyl)-5-cis-13-trans-ω-tetranorprostadienoic acid (34c) weighing 18 mg was collected. The ir spectrum exhibited strong carbonyl absorbtion at 1660 cm$^{-1}$ and 1610 cm$^{-1}$ for the enone and broad hydroxy absorbtion at (3650–3200 cm$^{-1}$).

EXAMPLE XXXI

2-[5α-hydroxy-2β-(3-oxo-4-(m-tolyl)but-1-yl)cyclopent-1α-yl]acetic acid, γ-lactone (6c).

A heterogeneous mixture of 6.8 g of 2-[5α-hydroxy-2β-(3-oxo-4-(m-tolyl)-trans-buten-1-yl)cyclopent-1α-yl]acetic acid, γ-lactone (2c) and 670 mg of 10% palladium on carbon in 55 ml of ethyl acetate was shaken in a Parr Shaker for 30 minutes. The mixture was then filtered through a pad of Celite and was concentrated. Purification of the crude residue by silica gel chromatography using 10% ethyl acetate in benzene as eluent afforded the desired 2-[5α-hydroxy-2β-(3-oxo-4-(m-tolyl)but-1-yl(cyclopenta-1α-yl)]acetic acid, γ-lactone (6c) as a solid melting at 60.5°–62.5° and weighing 2.9 g.

The product of this invention (6c) may be converted into the 13,14-dihydro prostaglandin two-series analogs by the procedures of Examples XVI–XXI, XXIII, XXVI–XXX and XXXIV–XXXV.

EXAMPLE XXXII

2-[5α-hydroxy-2β-(3α-(tetrahydropyran-2-yloxy)-4-phenylbut-1-yl)cyclopent-1α-yl]acetic acid, γ-lactone (8b).

A heterogeneous mixture of 500 mg of 2-[5α-hydroxy-2β-(3α-(tetrahydropyran-2-yloxy)-4-phenyl-trans-buten-1-yl)cyclopent-1α-yl]acetic acid, (4b) and 50 mg of 5% rhodium on alumina in 5 ml of ethyl acetate is stirred under 1 atmosphere of hydrogen for 2 hours. The mixture then is filtered through a pad of Celite then is concentrated. Purification of the crude residue by silica gel chromatography affords the desired 2-[5α-hydroxy-2β-(3α-(tetrahydropyran-2-yloxy)-4-phenylbut-1-yl)cyclopent-1α-yl]acetic acid, γ-lactone (8b).

The product of this example (8b) may be converted into the 13,14-dihydroprostaglandin two-series analogs by the procedures of Examples XXVIII–XXI, XXIII, XXVI–XXX, and XXXIV–XXXV.

EXAMPLE XXXIII

2-[5α-hydroxy-2β-(3α-dimethyl-tert-butylsilyloxy-4-(3,5-dimethylphenyl)-trans-buten-1-yl)cyclopenta-1α-yl]acetic acid, γ-lactone (4d).

A solution of 1.47 g (4.95 mmoles) of 2-[5α-hydroxy-2β-(3α-hydroxy-4-(3,5-dimethylphenyl)-trans-buten-1-yl)cyclopent-1α-yl]acetic acid, γ-lactone (3d), 945 mg (6.3 mmoles) of dimethyl-tert-butylsilyl chloride, and 910 mg (13.4 mmoles) of imidazole in 2.5 ml of dimethylformamide was stirred under nitrogen at 37° for 18 hours. The solution was then concentrated, the residue was diluted with methylene chloride, and the organic layer was washed with water (3x), was dried (anhydrous magnesium sulfate), and was concentrated. Purification of the crude residue by silica gel chromatography using chloroform as eluent provided the desired 2-[5α-hydroxy-2β-(3α-dimethyl-tert-butylsilyloxy-4-(3,5-dimethylphenyl)-trans-buten-1-yl)cyclopent-1α-yl]acetic acid, γ-lactone (4d) as a viscous oil weighing 1.67 g.

The product of this example (4d) may be converted into the corresponding 11-desoxy prostaglandins by the procedures of Examples XVIII–XXX, XXXII, and XXXIV–XXXV.

EXAMPLE XXXIV p-Biphenyl (ent)-9-oxo-11-desoxy-15α-hydroxy-16-phenyl-cis-5-trans-13-ω-tetranorprostadienoate.

To a solution of 365 mg (1.02 mmole) of (ent)-9-oxo-11-desoxy-15α-hydroxy-16-phenyl-cis-5-trans-13-ω-tetranorprostadienoic acid in 40 ml of methylene chloride was added 11.7 ml of a 0.1 M solution of 1-(3-dimethylaminopropyl)-3-ethylcarbodiimide in methylene chloride. The solution was stirred under nitrogen for 18 hours then is concentrated. The residue was purified by silica gel chromatography using mixtures of benzene:chloroform as eluents to provide the desired p-biphenyl (ent)-9-oxo-11-desoxy-15α-hydroxy-16-phenyl-cis-5-trans-13-ω-tetranorprostadienoate as a white solid melting at 68°-70° and weighing 200 mg.

EXAMPLE XXXV n-Decyl (rac)-9-oxo-11-desoxy-15α-hydroxy-16-phenyl-cis-5-trans-ω-tetranorprostadienoate.

To a solution of 30 mg of (rac)-9-oxo-11-desoxy-15α-hydroxy-16-phenyl-cis-5-trans-ω-tetranorprostadienoic acid in 25 ml of ether was added a solution of diazodecane in ether (the reaction was followed by tlc using 10% methanol in methylene chloride as eluent: $R_f$ starting material 0.33, $R_f$ product 0.82). The solution was then concentrated and the crude product purified by column chromatography to provide the desired n-decyl (rac)-9-oxo-11-desoxy-15α-hydroxy-16-phenyl-cis-5-trans-ω-tetranorprostadienoate as a viscous oil weighing 5 mg.

Additional Compounds of the Structure

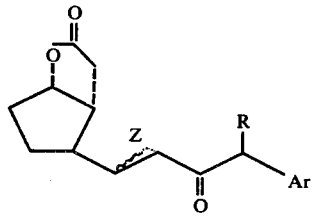

| Ar | Z* | R | mp | IR data cm$^{-1}$ | Rotation |
|---|---|---|---|---|---|
| m-methylphenyl | D | H | 80.5-82.5 | 1770, 1680, 1620, 980 | |
| o-biphenyl | D | H | 51°-52° | 1770, 1675, 1620, 980 | |
| 5-phenyl-2-thienyl | D | H | oil | 1775, 1700, 1680, 1640, 980 | |
| β-naphthyl (rac.) | D | H | oil | 1770, 1700, 1680, 1620, 970 | |
| p-chlorophenyl | D | H | oil | 1779, 1709, 1672, 1639, 980 | |
| p-t-butylphenyl | D | H | oil | 1770, 1695, 1675, 1635, 975 | |
| phenyl | D | (+)Me | oil | 1770, 1710, 1620, 975 | +112.1 (CHCl$_3$) |
| phenyl | D | (−)Me | 55°-58° | 1770, 1710, 1620, 975 | −32.79 (CHCl$_3$) |
| phenyl (ent) | D | H | oil | 1765, 1680, 1625, 975 | |
| 3,5-dimethyl | D | H | 110°-112° | 6.62, 6.13, 5.88, 10.35 (KBr in μ) | |

*D=trans double bond; S=single bond

Additional Compounds

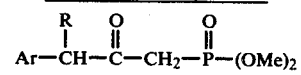

| Ar | R | bp/mp | Rotation | NMR (Jcps) |
|---|---|---|---|---|
| m-methylphenyl | H | 158°-162°/0.4mm | | 3.75 (11.5)*, 3.02 (22)** |
| o-biphenyl | H | purified by column chromatography | | 3.74 (11.5)*, 3.05 (22)** |
| 5-phenyl-2-thienyl | H | mp 64°-65° | | 3.75 (11.5)*, 3.08 (22)** |
| β-naphthyl | H | mp 45°-47° | | 3.73 (11.5)*, 3.10 (22)** |
| p-chlorophenyl | H | purified by column chromatography | | 3.76 (11.5)*, 3.15 (22)** |
| p-t-butylphenyl | H | 180°-/0.2 mm | | 3.74 (11.5)*, 3.11 (22)** |
| phenyl | (+)Me | purified by column chromatography | +205(CHCl$_3$) | 3.78 (11.5)*, 3.26 (22)** <br> 3.71 (11.5)*, 2.93 (22)** |
| phenyl | (−)Me | purified by column chromatography | −233(CHCl$_3$) | 3.78 (11.5)*, 3.26 (22)** <br> 3.71 (11.5)*, 2.93 (22)** |
| 3,4-dichlorophenyl | H | 185°-188°/0.2 mm | | 3.77 (11.5)*, 3.16 (22)** |
| 3,5-dimethylphenyl | H | 174°/0.3 mm | | 3.82 (11.5)*, 3.14 (22)** |

*methoxy protons

**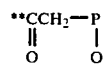

Additional Compounds

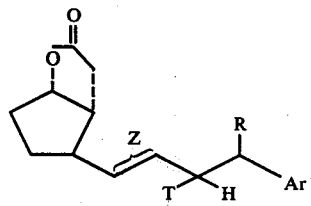

| Ar | R | T | Z[a] | Polarity[b] | SS[c] | IR data cm$^{-1}$ |
|---|---|---|---|---|---|---|
| m-methylphenyl | H | α-OH | D | LP | Hφ/Et$_2$O | 1770, 970, 3600 |
| m-methylphenyl | H | β-OH | D | MP | | 1770, 970, 3600 |
| o-biphenyl | H | α-OH | D | LP | Hφ/Et$_2$O | 1770, 975, 3600 |
| o-biphenyl | H | β-OH | D | MP | | 1770, 975, 3600 |
| 5-phenyl-2-thienyl | H | α-OH | D | LP | Hφ/Et hd 2O | 1770, 975, 3600 |
| 5-phenyl-2-thienyl | H | β-OH | D | MP | | 1770, 970, 3600 |
| β-naphthyl | H | α-OH | D | LP | Hφ/Et$_2$O | 1770, 970, 3598 |
| β-naphthyl | H | β-OH | D | MP | | 1770, 970, 3598 |
| p-chlorophenyl | H | α-OH | D | LP | Hφ/Et$_2$O | 1770, 970, 3598 |
| p-chlorophenyl | H | β-OH | D | MP | | 1770, 970, 3598 |
| p-t-butylphenyl | H | α-OH | D | LP | Hφ/Et$_2$O | 1770, 970, 3598 |
| p-t-butylphenyl | H | β-OH | D | MP | | 1770, 970, 3598 |
| phenyl | (+)Me | α-OH | D | LP | 10%EtoAc/Benzene | 1770, 970, 3600 |
| phenyl | (+)Me | β-OH | D | MP | " | 1770, 970, 3600 |
| phenyl | (−)Me | α-OH | D | LP | 20%Et$_2$O/Benzene | 1770, 970, 3600 |
| phenyl | (−)Me | β-OH | D | MP | " | 1770, 970, 3600 |
| phenyl (ent) | H | α-OH | D | LP | Et$_2$O/cyclohexane | 1760, 960, 3600 |
| phenyl (ent) | H | β-OH | D | MP | | 1760, 960, 3600 |
| 3,5-dimethylphenyl | H | α-OH | D | LP | Hφ/EtoAc | 1770, 975, 3550 |
| 3,5-dimethylphenyl | H | β-OH | D | LP | | 1770, 975, 3550 |

[a]D is trans double bond; S is single bond
[b]TLC mobility LP=less polar, MP=more polar
[c]Solvent system for column chromatography isomer separation

Additional Compounds

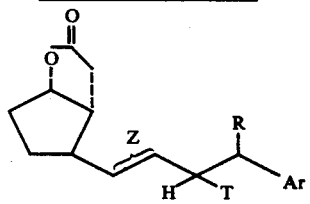

| Ar | T | R | Z* | IR data cm$^{-1}$ |
|---|---|---|---|---|
| m-methylphenyl | α-OTHP | H | D | 1770, 970 |
| m-methylphenyl | β-OTHP | H | D | 1770, 970 |
| o-biphenyl | α-OTHP | H | D | 1770, 970 |
| o-biphenyl | β-OTHP | H | D | 1770, 970 |
| 5-phenyl-2-thienyl | α-OTHP | H | D | 1770, 970 |
| 5-phenyl-2-thienyl | β-OTHP | H | D | 1770, 970 |
| β-naphthyl | α-OTHP | H | D | 1770, 970 |
| β-naphthyl | β-OTHP | H | D | 1770, 970 |
| p-chlorophenyl | α-OTHP | H | D | 1770, 970 |
| p-chlorophenyl | β-OTHP | H | D | 1770, 970 |
| p-t-butylphenyl | α-OTHP | H | D | 1770, 970 |
| p-t-butylphenyl | β-OTHP | H | D | 1770, 970 |
| phenyl | α-OTHP | (+)Me | D | 1770, 970 |
| phenyl | β-OTHP | (+)Me | D | 1770, 970 |
| phenyl | α-OTHP | (−)Me | D | 1770, 970 |
| phenyl | β-OTHP | (−)Me | D | 1770, 970 |
| phenyl (ent) | α-OTHP | H | D | 1760, 960 |
| phenyl (ent) | β-OTHP | H | D | 1760, 960 |
| 3,5-dimethylphenyl | α-ODMTBS | H | D | 1760, 965 |
| 3,5-dimethylphenyl | β-ODMTBS | H | D | 1760, 965 |

*D is trans double bond; S is single bond.

Additional Compounds

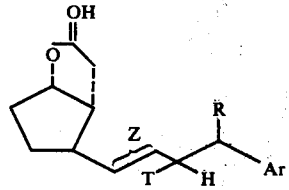

| Ar | T | R | Z* | IR data cm$^{-1}$ |
|---|---|---|---|---|
| m-methylphenyl | α-OTHP | H | D | 970 |
| m-methylphenyl | β-OTHP | H | D | 970 |
| o-biphenyl | α-OTHP | H | D | 970 |
| o-biphenyl | β-OTHP | H | D | 970 |
| 5-phenyl-2-thienyl | α-OTHP | H | D | 970 |
| 5-phenyl-2-thienyl | β-OTHP | H | D | 970 |
| β-naphthyl | α-OTHP | H | D | 970 |
| β-naphthyl | β-OTHP | H | D | 970 |
| p-chlorophenyl | α-OTHP | H | D | 970 |
| p-chlorophenyl | β-OTHP | H | D | 970 |
| p-t-butylphenyl | α-OTHP | H | D | 965 |
| p-t-butylphenyl | β-OTHP | H | D | 965 |
| phenyl | α-OTHP | (+)Me | D | 975 |
| phenyl | β-OTHP | (+)Me | D | 975 |
| phenyl | α-OTHP | (−)Me | D | 975 |
| phenyl | β-OTHP | (−)Me | D | 975 |
| phenyl (ent) | α-OTHP | H | D | 970 |
| phenyl (ent) | β-OTHP | H | D | 970 |
| 3,5-dimethylphenyl | α-ODMTBS | H | D | 965 |
| 3,5-dimethylphenyl | β-ODMTBS | H | D | 965 |

*D is trans double bond; S is single bond.

Additional Compounds

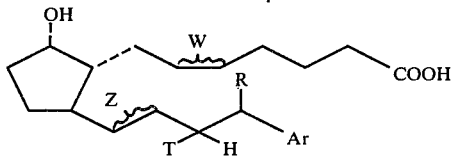

| Ar | T | R | W* | Z** | IR data cm⁻¹ |
|---|---|---|---|---|---|
| m-methylphenyl | α-OTHP | H | D | D | nmr consistent |
| m-methylphenyl | β-OTHP | H | D | D | nmr consistent |
| o-biphenyl | α-OTHP | H | D | D | nmr consistent |
| o-biphenyl | β-OTHP | H | D | D | nmr consistent |
| 5-phenyl-2-thienyl | α-OTHP | H | D | D | nmr consistent |
| β-naphthyl | α-OTHP | H | D | D | nmr consistent |
| β-naphthyl | β-OTHP | H | D | D | nmr consistent |
| p-chlorophenyl | α-OTHP | H | D | D | nmr consistent |
| p-chlorophenyl | β-OTHP | H | D | D | nmr consistent |
| p-t-butylphenyl | α-OTHP | H | D | D | 1710, 970 |
| p-t-butylphenyl | β-OTHP | H | D | D | 1710, 970 |
| phenyl | α,β-OTHP | (+)Me | D | D | 1705, 965 |
| phenyl | α,β-OTHP | (−)Me | D | D | 1705, 965 |
| phenyl (ent) | α-OTHP | H | D | D | 1700, 965 |
| phenyl (ent) | β-OTHP | H | D | D | 1700, 965 |

*D is cis double bond; S is single bond.
**D is trans double bond; S is single bond.

Additional Compounds

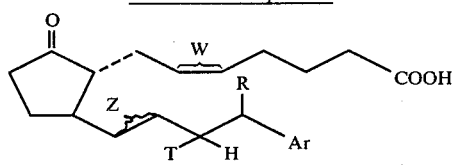

| Ar | T | R | W* | Z** |
|---|---|---|---|---|
| m-methylphenyl | α-OTHP | H | D | D |
| m-methylphenyl | β-OTHP | H | D | D |
| o-biphenyl | α-OTHP | H | D | D |
| o-biphenyl | β-OTHP | H | D | D |
| 5-phenyl-2-thienyl | α-OTHP | H | D | D |
| β-naphthyl | α-OTHP | H | D | D |
| β-naphthyl | β-OTHP | H | D | D |
| p-chlorophenyl | α-OTHP | H | D | D |
| p-chlorophenyl | β-OTHP | H | D | D |

Additional Compounds -continued

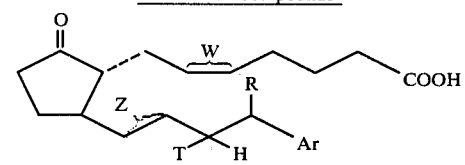

| Ar | T | R | W* | Z** |
|---|---|---|---|---|
| p-t-butylphenyl | α-OTHP | H | D | D |
| p-t-butylphenyl | β-OTHP | H | D | D |
| phenyl | α-OTHP | (+)Me | D | D |
| phenyl | β-OTHP | (+)Me | D | D |
| phenyl | α,β-OTHP | (−)Me | D | D |
| phenyl (ent) | α-OTHP | H | D | D |
| phenyl (ent) | β-OTHP | H | D | D |

*D is cis double bond; S is single bond.
**D is trans double bond; S is single bond.

Additional Compounds

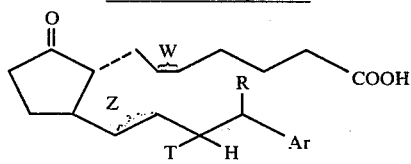

| Ar | T | R | W* | Z** | IR data cm⁻¹ |
|---|---|---|---|---|---|
| m-methylphenyl | α-OH | H | D | D | consistent nmr |
| m-methylphenyl | β-OH | H | D | D | consistent nmr |
| o-biphenyl | α-OH | H | D | D | 1735, 1710, 975 |
| o-biphenyl | β-OH | H | D | D | consistent nmr |
| 5-phenyl-2-thienyl | α-OH | H | D | D | |
| β-naphthyl | α-OH | H | D | D | 1730, 1705, 960 |
| β-naphthyl | β-OH | H | D | D | 1735, 1710, 965 |
| p-chlorophenyl | α-OH | H | D | D | 1730, 1710, 970 |
| p-chlorophenyl | β-OH | H | D | D | 1730, 1710, 970 |
| p-t-butylphenyl | α-OH | H | D | D | 1730, 1715, 970 |
| p-t-butylphenyl | β-OH | H | D | D | 1730, 1715, 970 |
| phenyl | α-OH | (+)Me | D | D | 1730, 1705, 970 |
| phenyl | β-OH | (+)Me | D | D | 1730, 1705, 970 |
| phenyl | α-OH | (−)Me | D | D | 1730, 1710, 965 |
| phenyl | β-OH | (−)Me | D | D | 1730, 1710, 965 |
| phenyl (ent) | α-OH | H | D | D | 1730, 1710, 960 |
| phenyl (ent) | β-OH | H | D | D | 1730, 1710, 960 |
| phenyl | β-OH | H | D | S | 1735, 1710 |
| 3,4-dimethoxyphenyl | α-OH | H | S | S | 1730, 1710, 965 |

-continued

Additional Compounds

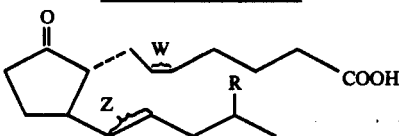

| Ar | T | R | W* | Z** | IR data cm$^{-1}$ |
|---|---|---|---|---|---|
| o-methylphenyl | α-OH | H | S | S | 1730, 1715 |

*D is cis double bond; S is single bond.
**D is trans double bond; S is single bond.

Additional Compounds

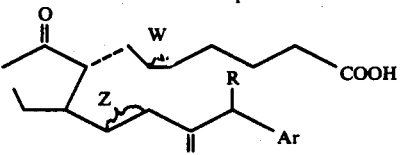

| Ar | R | W* | Z** | IR data cm$^{-1}$ |
|---|---|---|---|---|
| β-naphthyl | H | D | D | consistent nmr |
| phenyl | H | D | D | 1735, 1700, 1680, 1625, 970 |
| phenyl | (+)Me | D | D | 1735, 1700, 1670, 1625, 975 |
| o-biphenyl | H | D | D | consistent nmr |

*D is cis double bond; S is single bond.
**D is trans double bond; S is single bond.

What is claimed is:
1. A compound of the structure:

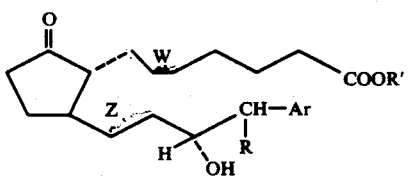

wherein Ar is α- or β-naphthyl; phenyl; 3,4-dimethoxyphenyl; 3,4-methylenedioxyphenyl; 3,4-dichlorophenyl; 3,5-dimethyl and monosubstituted phenyl wherein said substituent is bromo, chloro, fluoro, trifluoromethyl, phenyl, lower alkyl or lower alkoxy; R is hydrogen;
and wherein R' is hydrogen;
alkyl of from 1-10 carbon atoms; aralkyl of from 7 to 9 carbon atoms; α- or β-naphthyl; phenyl or substituted phenyl wherein said substituent is lower alkyl, lower alkoxy, chloro, bromo, fluoro or phenyl and wherein W is a single bond; and
Z is a single bond.
2. A compound of the structure:

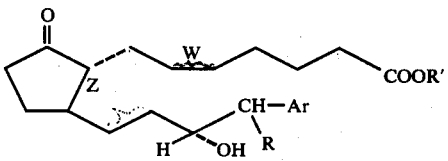

wherein Ar is α- or β-naphthyl; phenyl; 3,4-dimethoxyphenyl; 3,4-methylenedioxyphenyl; 3,4-dichlorophenyl; 3,5-dimethylphenyl and monosubstituted phenyl wherein said substituent is bromo, chloro, fluoro, trifluoromethyl, phenyl, lower alkyl or lower alkoxy; R is hydrogen;
and wherein R' is hydrogen;
alkyl of from 1-10 carbon atoms; aralkyl of from 7 to 9 carbon atoms; α- or β-naphthyl; phenyl or substituted phenyl wherein said substituent is lower alkyl, lower alkoxy, chloro, bromo, fluoro or phenyl and wherein
W is a cis double bond; and
Z is a single bond.
3. The compound of claim 1, 11-desoxy-16-phenyl-ω-tetranorprostaglandin E$_0$.
4. The compound of claim 2, 11-desoxy-13,14-dihydro-16-phenyl-ω-tetranorprostaglandin E$_2$.
5. The compound of the formula

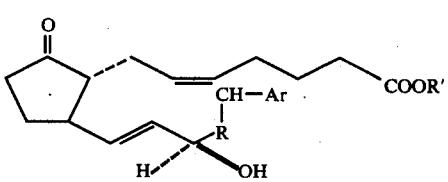

wherein Ar is m-tolyl and R and R' are each hydrogen.